US 8,449,812 B2

(12) United States Patent
Hasenzahl et al.

(10) Patent No.: US 8,449,812 B2
(45) Date of Patent: May 28, 2013

(54) PROCESS FOR THE PRODUCTION OF A TITANIUM SILICALITE SHAPED ARTICLE

(75) Inventors: Steffen Hasenzahl, Hanau (DE); Ralf Jantke, Mömbris (DE)

(73) Assignee: Evonik Degussa AG, Essen (DE)

( * ) Notice: Subject to any disclaimer, the term of this patent is extended or adjusted under 35 U.S.C. 154(b) by 1143 days.

(21) Appl. No.: 10/204,306

(22) PCT Filed: Mar. 21, 2001

(86) PCT No.: PCT/EP01/03239
§ 371 (c)(1),
(2), (4) Date: Oct. 15, 2002

(87) PCT Pub. No.: WO01/72420
PCT Pub. Date: Oct. 4, 2001

(65) Prior Publication Data
US 2003/0130116 A1    Jul. 10, 2003

(30) Foreign Application Priority Data
Mar. 29, 2000    (EP) .................................. 00106670

(51) Int. Cl.
*B28B 1/00*    (2006.01)

(52) U.S. Cl.
USPC ........................... 264/621; 264/623; 502/242

(58) Field of Classification Search
USPC .................... 502/242; 264/621, 623
See application file for complete search history.

(56) References Cited

U.S. PATENT DOCUMENTS

| | | | |
|---|---|---|---|
| 2,326,059 A * | 8/1943 | Nordberg | 501/94 |
| 4,410,501 A | 10/1983 | Taramasso et al. | |
| 4,908,432 A | 3/1990 | Yip | |
| 5,156,829 A * | 10/1992 | McCullen et al. | 423/718 |
| 5,384,418 A * | 1/1995 | Zajacek et al. | 549/531 |
| 5,430,000 A | 7/1995 | Timken | |
| 5,525,563 A | 6/1996 | Thiele et al. | |
| 5,595,715 A * | 1/1997 | Roth | 423/328.1 |
| 5,637,715 A | 6/1997 | Thiele et al. | |
| 5,712,402 A * | 1/1998 | Pinnavaia et al. | 552/309 |
| 5,756,778 A | 5/1998 | Thiele et al. | |
| 5,762,902 A * | 6/1998 | Benazzi et al. | 423/700 |
| 5,882,624 A * | 3/1999 | Kuznicki et al. | 423/700 |
| 5,885,546 A | 3/1999 | Kumar et al. | 423/703 |
| 5,919,430 A | 7/1999 | Hasenzahl et al. | |
| 5,958,366 A * | 9/1999 | Smith et al. | 423/700 |
| 5,977,009 A * | 11/1999 | Faraj | 502/64 |
| 6,008,389 A * | 12/1999 | Grosch et al. | 549/533 |
| 6,054,112 A | 4/2000 | Hasenzahl et al. | |
| 6,106,803 A | 8/2000 | Hasenzahl et al. | |
| 6,189,340 B1 * | 2/2001 | Burke et al. | 65/399 |
| 2003/0078160 A1 * | 4/2003 | Hasenzahl et al. | 502/242 |

FOREIGN PATENT DOCUMENTS

| | | |
|---|---|---|
| BE | 1001038 | 3/1990 |
| DE | 196 23 611 | 12/1997 |
| DE | 196 23 972 | 12/1997 |
| DE | 197 31 627 A1 | 1/1999 |
| DE | 198 39 792 | 3/2000 |
| EP | 0 325 053 | 7/1989 |
| EP | 0 659 685 A1 | 6/1995 |
| EP | 0 791 558 | 8/1997 |
| EP | 0 893 148 | 1/1999 |
| EP | 0 906 784 A2 | 4/1999 |
| EP | 0 906 784 A3 | 3/2000 |
| FR | 2 471 950 | 6/1981 |
| WO | WO 96/16004 A2 | 5/1996 |
| WO | WO 98/55229 A1 | 12/1998 |
| WO | WO 99 28030 | 6/1999 |
| WO | WO 99/52626 | 10/1999 |
| WO | WO 00/12432 A1 | 3/2000 |

OTHER PUBLICATIONS

Thangaraj, A. et al, "Studies on the Synthesis of Titanium Silicalite. TS-1," Zeolites. 1992. pp. 943-950. vol. 12, Nov./Dec. issue, Butterworth-Heinemann, USA. 8 pages.
Thangaraj, A. et al., "Catalytic Properties of Crystalline Titanium Silicalites." Journal of Catalysis 1991, pp. 1-8, vol. 130, Academic Press, Inc., USA. 8 pages.
Zhang. G. et al., "Preparation of Colloidal Suspensions of Discrete Ts-1 Crystals." Chemistry of Materials, 1997, pp. 210-217, vol. 9. No. 1, American Chemical Society. Washington. D.C. USA. 8 pages.
Satterfield, C. N., "Heterogenous Catalysis in Industrial Practise," 2nd ed., McGraw-Hill, Inc. (1991), p. 97-99.

* cited by examiner

*Primary Examiner* — John Hoffmann
(74) *Attorney, Agent, or Firm* — Smith, Gambrell & Russell, LLP

(57) ABSTRACT

A process for the production of a titanium silicalite shaped article by: a) preparation of a synthesis gel containing a $Si_2$ source, a $Ti_2$ source, a template compound and water, b) crystallization of the synthesis gel under hydrothermal conditions, c) drying of the titanium silicalite from step b) at a temperature below the decomposition temperature of the template compound, d) preparation of a formable mass containing the product from step c), a binder and a paste-forming agent, e) forming of the mass from step d) into a green shaped article, f) optionally drying, and g) calcinations of the green shaped article, as well as a titanium silicalite shaped article obtainable according to this process, and the use of this shaped article as a catalyst in epoxidation or ammoximation reactions.

13 Claims, No Drawings

PROCESS FOR THE PRODUCTION OF A TITANIUM SILICALITE SHAPED ARTICLE

The present invention relates to a process for the production of a titanium silicalite shaped article, a titanium silicalite shaped article obtainable according to the aforedescribed process, and a process for the epoxidation of olefins as well as for the ammoximation of ketones using this titanium silicalite shaped article.

A process for the production of titanium silicalite as well as for the use of the titanium silicalite thus produced as a catalyst in a number of reactions, including inter alia oxidation reactions, is known from U.S. Pat. No. 4,410,501. The production of the titanium silicalite is effected by forming a synthesis gel starting from a hydrolysable silicon compound such as for example tetraethyl orthosilicate and a hydrolysable titanium compound by addition of tetra-n-propyl ammonium hydroxide, followed by hydrolysis and crystallisation of this reaction mixture. After completion of the crystallisation the crystals are separated by filtration, washed, dried and finally calcined for 6 hours at 550° C.

In DE-A 197 31 672 a process is described for the production of titanium silicalite granules, whereby a synthesis gel that contains a $SiO_2$ source, a $TiO_2$ source, a compound containing tetra-n-propyl ammonium ions, a base and water is crystallised under hydrothermal conditions and the titanium silicalite suspension thus obtained is subjected without prior separation to a spray drying or to a fluidised bed spray granulation drying, following which the formed titanium silicalite granules are calcined at a temperature from 400° C. to 1,000° C., preferably from 500° C. to 750° C.

Particularly when using the catalyst in a fixed bed for the epoxidation of olefins or the ammoximation of ketones, the desired aim is to form fairly large shaped articles that have a sufficient hardness and abrasion resistance so that the physical integrity of the catalyst shaped articles is retained even after prolonged use. In particular the formation of fines, which are extracted with the reaction product and on the one hand lead to catalyst losses and on the other hand necessitate a relatively complicated separation of the reaction products, should be reduced or avoided.

From DE-A 196 23 611 a process for the production of titanium silicalite shaped articles is known, according to which first of all a synthesis gel is produced by hydrolysis of a silicon source, a titanium source and tetra-n-propyl ammonium hydroxide, this synthesis gel is crystallized under hydrothermal conditions, and the resultant solid is separated for example by centrifugation, dried and then calcined at 550° C. This calcined titanium silicalite powder is then processed further by addition of water, binders such as for example silica sol, and plasticisers such as methyl cellulose, to form a plastic mass that is extruded into strands, the said strands then being dried and calcined once more for 5 hours at 500° C. The strands are then comminuted into granules or crushed material having a grain size of between 1 and 10 mm.

WO 98/55229 discloses a comparable process in which the formable mass is prepared by adding a mixture of water and alcohol as paste-forming agent.

All these processes known from the prior art have in common the feature that the titanium silicalite that is formed after the hydrothermal crystallisation is calcined before carrying out further forming steps, and after forming has been carried out the resulting shaped article is calcined a second time. The object of the present invention is accordingly to provide a process for the production of titanium silicalite shaped articles that is more efficient and cost-effective compared to the processes of the prior art, without however adversely affecting the desired properties of the titanium silicalite shaped articles as catalysts in oxidation reactions of olefins and/or in the ammoximation of ketones. A further object of the present invention is to provide a titanium silicalite shaped article having improved properties.

SUMMARY OF THE INVENTION

This object is achieved by a process for the production of a titanium silicalite shaped article by
a) preparation of a synthesis gel containing a $SiO_2$ source, a $TiO_2$ source, a template compound and water,
b) crystallization of the synthesis gel under hydrothermal conditions,
c) drying of the titanium silicalite from step b) at a temperature below the decomposition temperature of the template compound,
d) preparation of a formable mass containing the product from step c), a binder and a paste-forming agent,
e) forming of the mass from step d) into a green shaped article,
f) optionally drying, and
g) calcination of the green shaped article,
as well as by a titanium silicalite shaped article obtainable according to this process.

In contrast to the processes according to the prior art, the solids from the crystallisation step of the titanium silicalite synthesis are dried at a temperature below the decomposition temperature of the template compound, preferably at a temperature in the range from 50 to less than 400° C., and the dried but still not yet calcined product is then subjected to a shaping step.

The calcination is in general a very energy-intensive step since it is carried out at high temperatures in the range from 400° C. to 1,000° C., in particular from 500° C. to 750° C., for several hours, as a rule from 3 to 15 hours, preferably 3 to 6 hours. Since the process according to the invention simply involves a calcination step after the formation of the green shaped article, it is substantially less energy-intensive and thus significantly more cost-effective compared to the prior art. Moreover it was surprisingly found that the desired properties of the catalyst shaped article produced in this way, such as catalytic activity and selectivity for olefin oxide in an epoxidation reaction of olefins, is not adversely affected, and indeed the mechanical properties, such as for example the breaking hardness, may even be improved. Accordingly a titanium silicalite shaped article that has an improved breaking hardness and is thus suitable in particular as a catalyst packing for fixed bed reactors for use in the epoxidation of olefins can be obtained by the process according to the invention.

DETAILED DESCRIPTION OF THE INVENTION

According to one embodiment of the process according to the invention the crystal suspension that is formed after the hydrothermal crystallisation is subjected to a solid-liquid separation process, such as for example centrifugation or filtration, in order to separate the resultant titanium silicalite crystallites. The separated solid material is then preferably washed several times and dried at a temperature below the decomposition temperature of the template compound.

However, difficulties may arise in the filtration, particularly with titanium silicalite crystal suspensions containing crystallite agglomerations of small grain sizes. Accordingly filters for example with small pore sizes then have to be used, which result in particular in longer filtration times and high pressure losses during the filtration, thereby adversely affecting the efficiency of the filtration. This disadvantage can be circumvented on the one hand by neutralising the crystal suspension. The crystal suspension that is formed after the end of the crystallisation is alkaline on account of the excess of basic template compound and as a rule has a pH of >12. If the pH of the suspension is reduced to a value of 7 to 10, preferably 7 to 8.5, a more marked agglomeration of the primary crystallites is observed. The filterability of the suspension is thereby greatly improved, with the result that the separation can be carried out with standard membrane filters without disintegration of the product, and with conventional filtration times. The efficiency of the process according to the invention can thus be improved even further with this preferred embodiment.

In an alternative embodiment, which is particularly suitable for crystal suspensions that are difficult to filter, the crystal suspension is dried directly without prior separation of the solid material, at a temperature below the decomposition temperature of the template compound. In one embodiment of the invention spray drying is employed. The titanium silicalite granules that are thus produced consist of titanium silicalite crystals, silicon dioxide and titanium dioxide, wherein the content of silicon dioxide may be between 1 and 10 wt. % and the content of titanium dioxide may be between 0.05 and 1 wt. %. The granules produced by spray drying may have a diameter of between 5 and 300 μm and may be partially hollow.

As an alternative the crystallite suspension may also be dried by fluidised bed spray granulation drying.

In a preferred embodiment, in the direct drying of the crystal suspension from the hydrothermal step the solids content may be increased before the spray drying or the fluidized bed spray granulation drying so that the solids content of the titanium silicalite suspension is preferably at least 50 wt. %. To this end the titanium silicalite suspension obtained after the crystallization may for example be divided and the solid material may be separated from one part of the suspension by cake-forming filtration, centrifugation or other suitable methods, following which the filter cake or the sediment may then be suspended, optionally after a washing step, in the remaining part of the titanium silicalite-1 suspension. In order to facilitate the separation of the solid material suitable flocculation aids may be added to the titanium silicalite suspension. The solids content of the titanium silicalite suspension may also be increased by evaporation, preferably under reduced pressure, or by cross-flow filtration. It is particularly preferred to concentrate the titanium silicalite suspension before the drying step since in this way the energy expenditure in relation to the mass of dried titanium silicalite can be reduced.

The spray drying or fluidised bed spray granulation drying that is advantageously used according to the present invention is described in more detail in DE 197 31 672, especially in the examples included therein.

An alternative embodiment relates to a process for the production of a titanium silicalite shaped article by:
 a) preparation of a synthesis gel containing a $SiO_2$ source, a $TiO_2$ source, a template compound and water,
 b) crystallizing the synthesis gel under hydrothermal conditions,
 c) concentration of the crystal suspension from step b),
 d) preparation of a formable mass containing the product from step c) and a binder,
 e) forming the mass from step d) into a green shaped article,
 f) optionally drying, and
 g) calcination of the green shaped article.

The concentration of the suspension in step c) may be carried out as in the embodiment described hereinbefore. The solids content of the titanium silicalite suspension after the concentration is preferably 10 to 50 wt. %. This embodiment has the additional advantage that the energy expenditure and the associated costs involved in the separation and drying of the titanium silicalite may also be reduced.

In the preparation of the synthesis gel before the crystallization of the titanium silicalite, a $SiO_2$ source, a $TiO_2$ source, a template compound as well as water are mixed together. Particularly suitable as starting compounds are hydrolyzable silicon compounds and hydrolyzable titanium compounds, which are then hydrolyzed in the presence of water. Suitable hydrolyzable silicon compounds and titanium compounds are the tetraalkyl orthosilicates and tetraalkyl orthotitanates, the alkyl preferably being chosen from the group comprising methyl, ethyl, propyl or butyl. The most preferred starting compounds are tetraethyl orthosilicate and tetraethyl orthotitanate. Template compounds are understood to be compounds that determine the crystal structure by their absorption into the crystal lattice of the product during the crystallization. Preferred template compounds are quaternary ammonium compounds such as tetraalkyl ammonium compounds, in particular a tetraalkyl ammonium hydroxide such as tetra-n-propyl ammonium hydroxide for the preparation of titanium silicalite-1 (MFI structure), tetra-n-butyl ammonium hydroxide for the preparation of titanium silicalite-2 (MEL structure) and tetraethyl ammonium hydroxide for the preparation of titanium-β-zeolite (DEA crystal structure).

The pH value of the synthesis gel of >9, preferably >11, necessary for the synthesis is established by the basic-reacting quaternary ammonium compound that is used as template. The temperature at which the synthesis gel is prepared may vary within wide limits; however, the mixture of silicon source and titanium source should preferably be cooled to a temperature in the range from 0° C. to 10° C., preferably 0° C. to 5° C., particularly preferably 1° C., following which the template compound is added in the form of an aqueous solution cooled to the same temperature.

In a further embodiment of the present invention, when using tetraalkyl orthosilicates and tetraalkyl orthotitanates respectively as silicon and titanium sources, the synthesis gel is heated to a temperature of 75° C. to 95° C. for a duration of 120 to 200 minutes and the alcohol that is formed is distilled off as an aqueous azeotrope in order to assist the hydrolysis of the hydrolysable titanium and silicon compounds. The synthesis gel is then crystallized under autogenous pressure optionally after an additional maturation time at a temperature of 150° C. to 220° C., preferably 170° C. to 190° C. Under these conditions the crystallization time is as a rule less than 3 days, preferably less than 24 hours.

Equally good starting compounds are silicon-titanium mixed oxides, which may be prepared for example by flame hydrolysis of a mixture of $SiCl_4$ and $TiCl_4$. These compounds may be dispersed in a suitable solution containing template and base, and crystallized as described above after an optional ageing stage and/or addition of inoculation crystals.

After the drying the titanium silicalite solids and the concentrated titanium silicalite suspension are processed with one or more binders, optionally with forming auxiliaries and optionally with a paste-forming agent, into a formable mass. In principle all substances known for such purposes are suitable as binders. Oxides of silicon, aluminum, boron, phosphorus, titanium, zirconium and/or manganese and the corresponding precursors are preferably used. Particularly preferred binders are silicon dioxides, aluminum oxides, titanium oxides and clay minerals, as well as mixtures thereof. Examples of silicon dioxides and silicon dioxide precursors are precipitated or fumed silicas, silica sols, tetraalkoxy silanes, partially condensed silicic acid esters and polysiloxanes, an example of an aluminum oxide is (pseudo) boehmite, examples of titanium dioxide are anatas or brookite, and examples of clay minerals are montmorillonites, kaolins, bentonites and sepiolites.

The binders may be used as a powder or in the form of sols, suspensions or solutions. The amount of binder is in general between 1 and 99 wt. %, preferably 5 to 60 wt. % and particularly preferably 10 to 40 wt. % referred to the solids content of the formable mass.

As forming auxiliaries there may be added substances that primarily promote the formation of a kneadable mass during the kneading, forming and drying step and that furthermore promote the mechanical stability of the shaped article during forming and drying. These substances are preferably removed during the calcination of the green shaped article. Organic viscosity-raising substances are preferred, such as for example cellulose, starch, acrylate, polyacrylate, polymethacrylate, polyvinyl alcohol, polyvinyl pyrollidone, polyisobutene and polytetrahydrofuran, polyglycol ethers, fatty acid compounds and/or wax emulsions.

Bases or acids may be added as further additives. Suitable compounds include for example ammonia, amines or quaternary ammonium salts, as well as carboxylic acids, such as for example formic acid, acetic acid or propionic acid. Obviously mixtures of two or more of the aforementioned additives may also be used.

Pore-forming agents such as polyalcohols, fructose, pentaerythritol, cellulose or sawdust may be used as further additives. These burn off during the calcination and leave behind additional mesopores and macropores in the shaped article.

Forming auxiliaries are used in the process according to the invention in an amount of 0 to 40 wt. %, preferably 1 to 10 wt. %, referred to the solids content of the formable mass.

As paste-forming agent there is preferably used in the process according to the invention an aqueous medium that optionally contains a water-miscible organic solvent. If an inorganic acid ester such as for example alkyl orthosilicate or alkyl orthotitanate is used as binder, then it is preferred to use as paste-forming agent a mixture of water and an alcohol that corresponds to the alcohol component of the inorganic acid ester. When using a mixture of alcohol and water as paste-forming agent, the alcohol content of this mixture is in general 1 to 80 wt. %, preferably 5 to 70 wt. % and particularly preferably 10 to 60 wt. %, in each case referred to the total weight of the mixture.

The paste-forming agent is used in amounts such that a plastic extrudable mass is formed, and is preferably used in an amount such that the solids content of the formable mass is 10 to 90 wt. %, preferably 60 to 80 wt. %.

Further suitable components may also be added to the formable mass, such as for example further zeolites, fumed or precipitated oxides and metals, as well as inorganic fibres to improve the mechanical stability, such as for example Al—Si fibres and/or Ca—Si fibres.

The order of addition of the constituents of the formable mass depends on a number of factors and has to be decided in each individual case. It is also possible first of all to add the binder to the titanium silicalite solid, then add the optionally used forming auxiliaries, and finally add the paste-forming agent. After the addition of the binder and optionally of the forming auxiliary the mass, which is as a rule still pulverulent, is homogenised in a kneader, extruder or mixer, and the paste-forming agent is then added. The resultant mixture is mixed until a plastic mass that can be extruded or formed into strands has been produced. In this connection the mixing is as a rule carried out at temperatures in the range from 10° C. up to the boiling point of the paste-forming agent, and under normal pressure, reduced pressure or slight super-atmospheric pressure.

In the embodiment that uses a concentrated titanium silicalite suspension as starting material, the binder and optionally forming auxiliary is preferably added to the titanium silicalite suspension and if necessary a paste-forming agent is additionally added in order to produce a kneadable mass.

All known mixing and forming equipment and processes may be used for the mixing and forming. Suitable known forming equipment is described for example in Ullmann's Encyclopaedia of Industrial Chemistry, 4$^{th}$ Edition, Vol, 2, p. 295 ff., 1972. Single-screw and twin-screw extruders or an extrusion press are preferably used. In this connection a large number of known geometries, such as for example full cylinders, hollow cylinders, stars, etc. may be produced. However, it is also possible to produce honeycomb structures.

The green shaped articles thus obtained, whose diameter is between 1 and 10 mm, may then be dried at room temperature or elevated temperatures, optionally in the presence of water vapour.

The shaped articles are next calcined in the presence of air, inert gas or oxygen in temperatures up to 1,100° C. The progress of the temperature over time, i.e. heating-up rate, holding times at the intermediate and final temperatures, as well as the cooling rate have to be optimised in each individual case. The calcination may serve to remove the template and the additives from the green shaped body and also decisively influences the mechanical stability, the pore volume or the specific surface.

The strands and/or extrudates that are obtained may be comminuted. In this connection they are preferably comminuted to granules or crushed material having a particle diameter of 0.1 to 5 mm, in particular 0.5 to 2 mm.

The following examples are given in order to illustrate the present invention:

REFERENCE EXAMPLE 1

Preparation of a titanium silicalite suspension

Tetraethyl orthosilicate, tetraethyl orthotitanate and tetra-n-propyl ammonium hydroxide in aqueous solution were mixed together and then hydrolysed in a 10 litre capacity autoclave under an inert atmosphere of nitrogen. The amounts were chosen so that the Si/Ti molar ratio was 35, the N/Si molar ratio was 0.17, and the $H_2O$/Si molar ratio was 27. After completion of the hydrolysis and distilling off the alcohol that was formed, which was replaced by an equal volume of water, the synthesis gel was crystallised for 3 hours at 175° C. under hydrothermal conditions. The titanium silicalite suspension thus obtained was worked up further in various ways according to the following examples and comparison examples.

EXAMPLE 1

The titanium silicalite suspension of reference example 1 was spray dried. 750 g of the titanium silicalite dried in this way, 20 g of methylhydroxycellulose and 200 g of aluminum oxide were weighed out and added to a 2.5 l kneader equipped with a discharge screw, mixed for 10 minutes, following which 30 g of glacial acetic acid were added. Water was then added within 20 minutes in such an amount that a compact mass was formed, which was then kneaded for a further 45 minutes. A constant taper screw was used for the extrusion. A mouthpiece with a corresponding bore was employed in the production of the 4 mm full cylinder. The extruded shaped articles were dried with a blower, then left to stand overnight in air, and finally calcined for 5 hours at 550° C.

The lateral breaking strength of the shaped article produced in this way was measured using a tablet breaking strength tester (TBH 28 Erweka). The mean value of a total of 20 measurements was 23 N.

EXAMPLE 2

823 g of spray dried titanium silicalite, 157 g of partially hydrolysed tetraethyl orthosilicate (Ester 40 from Wacker, 40 wt. % $SiO_2$) and 20 g of methylhydroxycellulose were placed in a kneader and mixed according to the procedure described in Example 1. Water was then added until a kneadable, formable mass had formed. This mass was kneaded for a further 45 minutes and was then extruded in a similar manner to that described in Example 1. The extruded shaped articles were dried as specified in Example 1 and then calcined for 1 hour at 550° C.

The calcined titanium silicalite shaped article had a lateral breaking strength of 58 N.

EXAMPLE 3

780 g of the spray dried titanium silicalite, 200 g of a clay mineral having the composition $Al_2O_3$ 18.55 wt. %, $SiO_2$ 74.98 wt. %, MgO 3.36 wt. %, BaO 1.42 wt. %, $Fe_2O_3$ 0.25 wt. % and $TiO_2$ 0.18 wt. % and 20 g of methylhydroxycellulose were placed in a kneader and mixed together according to the procedure described in Example 1. Water was then added within 20 minutes in such an amount that a compact mass was formed, which was kneaded for a further 45 minutes. The extrusion was carried out in a similar manner to Example 1 and the resulting extruded shaped articles were dried with a blower, then left to stand overnight in air, and finally dried for 1 hour at 550° C.

The calcined titanium silicalite shaped article had a lateral breaking strength of 19 N.

COMPARISON EXAMPLES 1 TO 3

The Examples 1 to 3 were repeated, except that the dried titanium silicalite shaped article was calcined for 5 hours at 550° C. before being processed further. The calcined shaped article according to comparison example 1 had a lateral breaking strength of 17 N. The lateral breaking strength of the calcined shaped article according to comparison example 3 was 14 N. The mass produced according to comparison example 2 was not extrudable and accordingly no shaped articles could be produced in this case.

EXAMPLE 4

The titanium silicalite suspension obtained in reference example 1 was concentrated to a solids content of 54 wt. % by distilling off the solvent (in particular water). 94.1 g of this suspension and 2.0 g of methylhydroxy-cellulose were placed in a 0.25 l capacity kneader and 38.0 g of spray dried titanium silicalite powder corresponding to Example 1 were slowly added. After further addition of 1.5 g of ammonium acetate and 20 g of the clay mineral according to Example 3 and 13 g of water, a soft and kneadable mass was formed, which was then kneaded for a further 2 hours. The readily extrudable mass was extruded in a similar manner to Example 1 and the resulting shaped articles were dried with a blower, left to stand overnight, and calcined for 1 hour at 550° C. in a chamber furnace.

The resulting calcined shaped article had a lateral breaking strength of 44 N.

A comparison of the examples according to the present invention and the comparison examples shows that on the one hand suitable catalyst shaped articles can be produced by the process according to the invention, all that is required being a calcination step after the formation of the green shaped articles, and thus compared to the prior art less energy is needed to produce a catalyst shaped article. Moreover these shaped articles have a significantly improved breaking hardness measured as lateral breaking strength, compared to the shaped articles that had been produced using calcined titanium silicalite powder as starting material.

Example 4 shows a particularly preferred embodiment, according to which after the concentration of the titanium silicalite suspension obtained from the hydrothermal step, this suspension is employed directly in the forming step. This process variant is particularly cost-effective since, compared to the prior art, in this case not only can a calcination step be avoided, but also the prior separation and drying of the titanium silicalite from the hydrothermal synthesis is no longer necessary. Surprisingly, with this process variant the breaking hardness of the resulting shaped articles was improved even further.

The invention claimed is:

1. Process for the production of a titanium silicalite shaped article comprising:
   a) preparing a synthesis gel containing a $SiO_2$ source, a $TiO_2$ source selected from the group consisting of tetraalkylorthotitanates and silicon-titanium mixed oxides obtainable by flame hydrolysis of a mixture of $SiCl_4$ and $TiCl_4$, a template compound and water,
   b) crystallizing the synthesis gel under hydrothermal conditions to obtain a crystal suspension containing titanium silicalite,
   c) drying the titanium silicalite from step b) at a temperature below the decomposition temperature of the template compound,
   d) preparing a formable mass containing a binder, a paste-forming agent and product from step c), said product being non-calcined and containing said template compound,
   e) forming of the mass from step d) into a green shaped article, said mass being not yet calcined,
   f) optionally drying, and
   g) calcining the green shaped article to thereby remove said template compound,
   characterized in that the template compound is chosen in a way that the titanium silicalite obtained by step b) exhibits MFI, MEL or β-zeolite structure and the calcination step takes place after the formation of the green shaped article.

2. Process according to claim 1, wherein said crystal suspension from step b) is optionally neutralized, and said titanium silicalite is separated using a solid-liquid separation process before step c).

3. Process according to claim 1, wherein said titanium silicalite from step b) is dried directly according to step c) without prior separation.

4. Process according to claim 3, wherein the process further comprises between steps b) and c) a step of distilling off volatile constituents or adding titanium silicalite or both.

5. Process according to claim 4, wherein the crystal suspension has a solids content before the drying step c) of at least 50 wt. %.

6. Process according to claim 1, wherein an aqueous medium that optionally contains a water-miscible organic solvent is used as said paste-forming agent.

7. Process according to claim 1, wherein the drying temperature in step c) is within the range of 50° to less than 400° C.

8. Process according to claim 1, wherein a compound of silicon, aluminum, boron, phosphorus, zirconium or titanium is used as said binder.

9. process according to claim 8, wherein the binder is selected from the group consisting of aluminum oxide, silicon oxide, hydrolysable silicon compounds and partial or total hydrolysates thereof, boron compounds, phosphorus compounds, clay minerals and mixtures thereof.

10. Process according to claim 1, wherein said calcining of the green shaped article takes place at a temperature from 400° C. to 1000° C.

11. The process according to claim 10 wherein said calcining takes place at a temperature of 500° C. to 750° C.

12. Process for the production of a titanium silicalite shaped article comprising:
   a) preparing a synthesis gel containing a $SiO_2$ source, a $TiO_2$ source selected from the group consisting of tetraalkylorthotitanates and silicon-titanium mixed oxides obtainable by flame hydrolysis of a mixture of $SiCl_4$ and $TiCl_4$, a template compound and water,
   b) crystallizing the synthesis gel under hydrothermal conditions to obtain a crystal suspension containing titanium silicalite,
   c) concentrating the crystal suspension from step b) to form a concentrated crystal suspension,
   d) preparing a formable mass containing the concentrated crystal suspension from step c) and a binder,
   e) forming of the formable mass from step d) into a green shaped article, said mass being not yet calcined,
   f) optionally drying, and
   g) calcining the green shaped article to thereby remove the template compound,
   characterized in that the template compound is chosen in a way that the titanium silicalite obtained by step b) exhibits MFI, MEL or β-zeolite structure and the titanium silicalite is not calcined prior to formation of the green shaped article.

13. Process according to claim 12, wherein said concentrated crystal suspension has a solids content after the concentration in step c) of 10-50 wt. %.

* * * * *